(12) United States Patent
Rozzell et al.

(10) Patent No.: US 7,550,277 B2
(45) Date of Patent: Jun. 23, 2009

(54) D-AMINO ACID DEHYDROGENASE AND METHOD OF MAKING D-AMINO ACIDS

(75) Inventors: David Rozzell, Burbank, CA (US); Scott J. Novick, Santa Clarita, CA (US)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 11/391,755

(22) Filed: Mar. 28, 2006

(65) Prior Publication Data

US 2008/0182972 A1 Jul. 31, 2008

Related U.S. Application Data

(60) Provisional application No. 60/666,035, filed on Mar. 28, 2005.

(51) Int. Cl.
C12P 13/04 (2006.01)
C12N 9/02 (2006.01)
C12N 9/04 (2006.01)

(52) U.S. Cl. .................. 435/106; 435/189; 435/190

(58) Field of Classification Search .................. None
See application file for complete search history.

(56) References Cited

U.S. PATENT DOCUMENTS

| 5,798,234 A | 8/1998 | Engel et al. |
| 2003/0207436 A1 | 11/2003 | Osabe et al. |

FOREIGN PATENT DOCUMENTS

| JP | 62 205790 A | 9/1987 |
| WO | WO 91/05870 A | 5/1991 |
| WO | WO 01/62948 A2 | 8/2001 |
| WO | WO 2005/017171 A2 | 2/2005 |

OTHER PUBLICATIONS

Bommarius, A. S. et al.; "Biocatalysis to amino acid-based chiral pharmaceuticals-examples and perspectives"; Journal of Molecular Catalysis B: Enzymatic 5; (1998); pp. 1-11.
Zhao, H. et al.; "Directed evolution of enzymes and pathways for industrial biocatalysis"; Current Opinion in Biotechnology; (2002): 13; pp. 104-110.
Farinas, E. T. et al.; "Directed enzyme evolution"; Current Opinion in Biotechnology; (2001); 12, pp. 545-551.
Uchiyama, H. et al.; "Directed Evolution to Improve the Thermostability of Prolyl Endopeptidase"; The Japanese Biochemical Society; (2000); vol. 128, No. 3; pp. 441-447.
Matsumura, I. et al.; "In vitro Evolution of Beta-glucuronidase into a Beta-galactosidase Proceeds Through Non-specific Intermediates"; J. Mol. Biol.; (2001); 305, pp. 331-339.
May, O. et al.; "Inverting enantioselectivity by directed evolution of hydantoinase for imroved production of L-methionine"; Nature Biotechnology; (2000); vol. 18, pp. 317-320.
Schmid, A. et al.; "The use of enzymes in the chemical industry in Europe"; Current Opinion in Biotechnology, (2002); 13; pp. 359-366.
Wakayama, M. et al.; "Production of D-amino acids by N-acyl-D-amino acid amidohydrolase and its structure and function"; Journal of Molecular Catalysis B: Enzymatic 23; (2003); pp. 71-85.
Mor, A. et al.; "Identification of a D-Alanine-containing Polypeptide Precursor for the Peptide Opioid, Dermorphin"; The Journal of Biological Chemistry; (1991); vol. 266, No. 10, Issue of Apr. 5, pp. 6264-6270.
Pritsker, M. et al.; "A synthetic all D-amino acid peptide corresponding to the N-terminal sequence of HIV-1 gp41 recognizes the wild-type fusion peptide in the membrane and inhibits HIV-1 envelope glycoprotein-mediated cell fusion"; Proc. National. Academy of Sciences USA; (1998) vol. 95, pp. 7287-7292.
Bommarius, A. S. et al.; "Comparison of Different Chemoenzymatic Process Routes to Enantiomerically Pure Acids"; Chimia 55; (2001); 50-59.
Pietzsch, M. et al.; "A New Racemase for 5-Monosubstituted Hydantoins"; Annals New York Academy of Sciences 672; (1992); pp. 478-483.
Cirilli, M. et al.; "The three-dimensional structure of the ternary complex of *Corynebacterium glutamicum* diaminopimelate dehydrogenase-NADPH-L-2-amino-6-methylene-pimelate"; Protein Science; (2000); 9:pp. 2034-2037.
Brunhuber, N. M. W. et al.; "The Biochemistry and Enzymology of Amino Acid Dehydrogenases"; Critical Reviews in Biochemistry and Molecular Biology; (1994); 29(6), pp. 415-467.
Krix, G. et al.; "Enzymatic reduction of α-keto acids leading to L-amino acids, D- or L-hydroxy acids"; Journal of Biotechnology; (1997); 53; pp. 29-39.
Cooper, A. J. .L. et al.; "Synthesis and Properties of the α-Keto Acids"; Chemical Reviews; (1983); vol. 83, No. 3, pp. 321-358.
Galkin, A. et al.; "Synthesis of Optically Active Amino Acids from α-Keto Acids with *Escherichia coli* Cells Expressing Heterologous Genes"; Applied and Environmental Microbiology; Dec. (1997); vol. 63, No. 12, pp. 4651-4656.
Vedha-Peters K., et al.; "Creation of a Broad-Range and Highly Stereoselective D-Amino Acid Dehydrogenase for the One-Step Synthesis of D-amino acids" Journal of the American Chemical Society; (2006); vol. 128, No. 33, pp. 10923-10929.
Kazlauskas, R.; "Engineering a multipurpose catalyst." Nature Chemical Biology; (Oct. 2006), vol. 2, No. 10, pp. 514-515.
International Search Report and Written Opinion from Applicants' counterpart PCT Application, No. PCT/US2006/011772.

*Primary Examiner*—Nashaat T Nashed
*Assistant Examiner*—MD. Younus Meah
(74) *Attorney, Agent, or Firm*—Christie, Parker & Hale, LLP.

(57) ABSTRACT

Polypeptides capable of catalyzing the reductive amination of a 2-ketoacid to its corresponding D-amino acid are provided. The polypeptides can be prepared by mutagenesis of, e.g., a diaminopimelate dehydrogenase. Also provided is a method of making a D-amino acid using a catalytically active polypeptide, wherein a 2-ketoacid is allowed to contact the polypeptide in the presence of a nicotinamide cofactor and ammonia or an ammonia source.

21 Claims, 9 Drawing Sheets

Ac—D-Nal—D-(*p*-Cl)-Phe—D-Pal—Ser—Tyr—D-Cit—Leu—Arg—D-Ala—NH$_2$

D-Nal = 3-(2-naphthyl)-D-alanine
D-(*p*-Cl)-Phe = *p*-chloro-D-phenylalanine
D-Pal = 3-(3-pyridyl)-D-alanine

D-AMINO ACID DEHYDROGENASE AND METHOD OF MAKING D-AMINO ACIDS

CROSS-REFERENCE TO RELATED APPLICATION(S)

This application claims priority of Provisional Application No. 60/666,035; filed Mar. 28, 2005, the entire contents of which are incorporated herein by reference.

ACKNOWLEDGEMENT OF GOVERNMENT SUPPORT

This invention was made in part with government support under Grant Number 1R43GM072107-01, awarded by the National Institutes of Health. The Government has certain rights in this invention.

BACKGROUND

This invention relates to catalytically active polypeptides and their use in making D-amino acids.

Unnatural or non-proteinogenic amino acids, which are structural analogs of the naturally-occurring amino acids that are the constituents of proteins, have important applications as pharmaceutical intermediates. For example, the anti-hypertensives ramipril, enalapril, benazapril, and prinivil are all based on L-homophenylalanine, and certain second generation pril analogs are synthesized from p-substituted-L homophenylalanine. Various β-lactam antibiotics use substituted D-phenylglycine side chains, and newer generation antibiotics are based on aminoadipic acid and other UAAs. The unnatural amino acids L-tert-leucine, L-nor-valine, L-nor-leucine, L-2-amino-5-[1,3]dioxolan-2yl-pentanoic acid, and the like have been used as a precursor in the synthesis of a number of different developmental drugs.

Unnatural amino acids are used almost exclusively as single stereoisomers. Since unnatural amino acids are not natural metabolites, traditional production methods for amino acids based on fermentation cannot generally be used since no metabolic pathways exist for their synthesis. Given the growing importance of unnatural amino acids as pharmaceutical intermediates, various methods have been developed for their enantiomerically pure preparation. Commonly employed methods include resolutions by diastereomeric crystallization, enzymatic resolution of derivatives, or separation by simulated moving bed (SMB) chiral chromatography. These methods can be used to separate racemic mixtures, but the maximum theoretical yield is only 50%.

In the case of non-proteinogenic L-amino acids such as L-nor-valine, L-nor-leucine, L-2-amino-5-[1-3]dioxolan-2-yl-pentanoic acid, L-tert-leucine, and many others, enzyme-catalyzed reductive amination is an effective method for their synthesis. Whereas the naturally-occurring alkyl and branched-chain amino acids can be produced by fermentation, taking advantage of the existing metabolic pathways to produce these amino acids, stereoselective production of non-proteinogenic analogs and various similar compounds is more difficult. The enzyme leucine dehydrogenase and mutants thereof have been shown to be capable of catalyzing the reductive amination of the corresponding 2-ketoacids of alkyl and branched-chain amino acids, and L-tert-leucine has been produced commercially with such an enzyme. A number of different reductive aminases for producing L-amino acids are commercially available currently (Enzyme catalog from BioCatalytics, Inc., Pasadena, Calif., March 2005).

However, to produce D-amino acids, enzyme-catalyzed reductive amination has not been an option in the past because enzymes catalyzing reductive amination of 2-ketoacids to produce D-amino acids have not been available. Accordingly, there is a need for novel mutant enzymes that catalyze the efficient reductive amination of a broad range of different 2-ketoacids to produce the corresponding D-amino acids, including D-counterparts of naturally-occurring amino acids and D-analogs of non-proteinogenic amino acids such as those listed above (D-nor-valine, D-nor-leucine, D-2-aminooctanoic acid, D-2-amino-5-[1,3]dioxolan-2yl-pentanoic acid, D-cyclohexylalanine, D-tert-leucine, and many others). There is also a need for new methods of making D-amino acids, using such mutant, D-amino acid dehydrogenase enzymes.

Optically pure D-amino acids are becoming increasingly important as pharmaceutically active compounds, chiral directing auxiliaries, and chiral synthons in organic synthesis. The largest current use of D-amino acids is in the production of semi-synthetic antibiotics. Ampicillin and amoxicillin (FIG. 1), made from D-phenylglycine and p-hydroxy-D-phenylglycine, respectively, are more broad-based and more stable to enzymatic degradation than naturally occurring (benzyl) penicillin. p-Hydroxy-D-phenylglycine is produced in a scale of several kilotons per year.

In addition to β-lactam antibiotics, D-amino acids are also found in antibacterial peptides. Table 1 lists several of these peptides along with the D-amino acids they contain.

TABLE 1

Antibacterial peptides and the D-amino acids they contain.

| Antibacterial peptide | D-Amino acid |
| --- | --- |
| Actinomycin D | D-Val |
| Bacitracin A | D-Glu, D-Phe, D-Orn, D-Asp |
| Circulin | D-Leu |
| Gramicidin S | D-Phe |
| Fungisporin | D-Phe, D-Val |
| Malformin B1a | D-Leu, D-Cys |
| Mycobacillin | D-Asp |
| Polymyxin B1 | D-Phe |
| Tyrocidine A | D-Phe |
| Valinomycin | D-Val |

The naturally occurring amphibian skin peptides dermorphin and dermenkephalin are another class of bioactive peptides containing D-amino acids (D-alanine and D-methionine, respectively). These peptides are highly potent morphine-like agonist.

D-Cyclohexylalanine, a component of the drug Inogatran (AstraZeneca), is another example of a D-amino acid found in a pharmaceutical product. Inogatran (FIG. 2) is a direct, low molecular weight thrombin inhibitor used to prevent blood-clot formation and, when coupled with other drugs, used to stimulate thrombolysis.

Cetrorelix (Degussa) is also a currently produced D-amino acid-containing drug, prescribed to those with fertility problems. This drug blocks the effects of Gonadotropin Releasing Hormone and prevents premature ovulation. Premature ovulation can lead to eggs that are not ready for fertilization. Cetrorelix is also being investigated (currently in clinical test phase II) for the treatment of endometriosis and uterine fibroids in women, and benign prostatic hypertrophy in men. This drug is a decapeptide containing five D-amino acids (FIG. 3).

Another peptide containing all D-amino acids is currently being investigated for the treatment of HIV. This peptide is able to bind to an HIV coat protein known as gp41. Once the peptide is bound to gp41, the HIV virus is unable to fuse to human cells, and thus the peptide limits the spread of the HIV virus within the body. This is an example of retro-reverso peptide, where target peptides are made using reversed sequences of only D-amino acids. Many highly bioactive, stable peptide analogs have been produced this way, including antibacterials, HIV fusion protein inhibitors, and synthetic vaccines.

D-Amino acids are also used in the fine chemical industry. For example, the pyrethroid insecticide Fluvalinate contains D-valine as a key building block (FIG. 4). Fluvalinate is a synthetic pyrethroid which is used as a broad spectrum insecticide against moths, beetles, and other insect pests on a variety of plants including cotton, cereal, grape, potato, fruit tree, vegetable and plantation crops, fleas, and turf and ornamental insects. It has both stomach and contact activity in target insects.

Current Methods:

There are currently three predominant methods to produce D-amino acids—enzymatic resolution of the racemate, enzymatic synthesis using a D-amino acid transaminase, and the conversion of hydantoins using the coupled enzymatic reactions of a D-hydantoinase and D-carbamoylase. All of three methods have drawbacks, however.

In the enzymatic resolution method (FIG. 5) both enantiomers are chemically acylated at the amine or esterified at the carboxylate followed by enzymatic hydrolysis of only one stereoisomer using either an amidase or esterase (e.g. lipase). After enantioselective hydrolysis, the two compounds can be separated to give the optically pure L- or D-amino acid. This method is limited to a maximum theoretical yield of 50% per cycle; in actual practice the yield is typically between 30-40%. The resolution process also involves multiple sequential reaction and purification steps which cannot be done in a single pot. Also, in some cases it can be difficult to find an enzyme that can selectively hydrolyze only one of the two modified amino acids, limiting the breadth of scope of this method.

In the D-transaminase reaction (FIG. 6), a method developed at BioCatalytics, Inc., an amine is donated from a starting D-amino acid (donor) to a 2-ketoacid to form the D-amino acid of interest and the corresponding 2-ketoacid of the donor amino acid. This reaction is catalyzed by a D-amino acid transaminase. The donor amino acid must be of the D-form but, since L-amino acids are much cheaper (e.g. L-aspartate is ~$3/kg), the transaminase reaction must be coupled with an amino acid racemase. This reaction can suffer from side reactions that generate byproducts, as the ketoacid formed from the donor amino acid can also be aminated. Special techniques are used to drive this reaction to completion. Typically L-aspartate is used as the donor and is converted to the D-antipode enzymatically; the 2-ketoacid formed, oxaloacetate, can spontaneously decarboxylate and drive the reaction (pyruvate is a poor amine acceptor). However, the decarboxylation step may not be sufficiently fast enough to keep up with the transaminase step, and yields and rates suffer in this case.

The D-hydantoinase/D-carbamoylase system (FIG. 7) starts with a racemate of hydantoins corresponding to the wanted amino acid. The conversion proceeds in two discrete steps. First, the D-hydantoin is selectively hydrolyzed to the D-carbamoylic acid with a D-hydantoinase, which is then hydrolyzed to the D-amino acid with a D-carbamoylase. The L-hydantoin will spontaneously racemize at a pH above 8, giving a theoretical yield of 100%. This method is currently used to make many D-amino acids; however, it does have some limitations. The conversion requires two types of enzymatic reactions that are difficult to carry out in a single pot, so two separate reactions and isolations are normally employed. This method is also dependent upon the spontaneous racemization of the hydantoin to achieve yields above 50%, and the rate of racemization is dependent on the substituent at the 5-position. This rate can vary greatly from $\tau_{1/2}$ of 0.3 h for phenylhydantoin (giving phenylalanine after hydrolysis), 5 h for benzylhydantoin (phenylglycine), 56 h for isopropylhydantoin (valine) and 120 h for tert-butylhydantoin (tert-leucine). Also, the substrate range of the D-hydantoinase and D-carbamoylase may not be broad enough to accept a wide range of substrate. Lastly, hydantoins are relatively insoluble in aqueous solution, limiting the titer of product that can be achieved.

Given the drawbacks of the three current methods for D-amino acid synthesis, there is clearly a need for a new method that reduces the number of steps necessary and increases the product yield.

SUMMARY OF THE INVENTION

The present invention provides novel polypeptides capable of catalyzing the conversion of a 2-ketoacid into its corresponding D-amino acid and genes encoding such novel polypeptides; methods of making and characterizing such polypeptides; and methods of making D-amino acids, including D-amino acids bearing alkyl, branched alkyl, aromatic, and heterocylic side chains, and also side chains that are neutral, acidic, or basic in nature. Nonlimiting examples of polypeptides capable of catalyzing the conversion of a 2-ketoacid to its corresponding D-amino acid include certain mutant diaminopimelate dehydrogenase (DAPDH) enzymes, and substantial equivalents thereof.

Thus, in a first aspect of the invention, an isolated, sequenced, polypeptide capable of catalyzing the conversion of a 2-ketoacid to its corresponding D-amino acid is provided. In one embodiment, the polypeptide comprises a modified amino acid sequence identified as SEQ ID NO. 4, or its substantial equivalent, wherein the modified amino acid sequence contains a replacement of at least one amino acid in SEQ ID NO. 4 selected from the group consisting of Lys44, Phe83, Thr89, Gln151, Asp155, Thr170, Glu178, Arg196, Pro244, His245, His248, and Asn271.

In another embodiment of the invention, a modified amino acid sequence identified as SEQ ID 4, or its substantial equivalent, is provided, wherein the modified amino acid sequence contains at least one amino acid replacement in SEQ ID NO. 4 selected from the group consisting of Lys44Glu, Phe83Ile, Thr89Pro, Gln151Leu, Asp155Gly, Thr170Ile, Thr170Val, Glu178Lys, Arg196Met, Pro244Ser, His245Asn, His248Glu, and Asn271Ser.

In still another embodiment of the invention, a modified amino acid sequence identified as SEQ ID NO. 2, or its substantial equivalent, is provided, wherein the modified amino acid sequence contains a replacement of at least one amino acid in SEQ ID NO. 2 selected from the group consisting of Lys43, Phe82, Thr88, Gln150, Asp154, Thr169, Glu177, Arg195, Pro243, His244, His247, and Asn270.

In yet another embodiment of the invention, a modified amino acid sequence identified as SEQ ID 2, or its substantial equivalent, is provided, wherein the modified amino acid sequence contains at least one amino acid replacement in SEQ ID NO. 2 selected from the group consisting of Lys43Glu, Phe82Ile, Thr88Pro, Gln150Leu, Asp154Gly, Thr169Ile, Thr169Val, Glu177Lys, Arg195Met, Pro243Ser, His244Asn, His247Glu, and Asn270Ser.

In another aspect of the invention, a method of making a D-amino acid is provided, and comprises contacting a 2-ketoacid with a polypeptide in the presence of a nicotinamide cofactor and ammonia or an ammonia source, the polypeptide being capable of catalyzing conversion of the 2-ketoacid into its corresponding D-amino acid. Preferably, the cofactor is utilized in its reduced form. In one embodiment, the polypeptide comprises a polypeptide having a modified amino acid sequence containing a replacement of at least one amino acid in SEQ ID NO. 4 selected from the group consisting of Lys44, Phe83, Thr89, Gln151, Asp155, Thr170, Glu178, Arg196, Pro244, His 245, His248, and Asn271.

The invention also provides oligonucleotide sequences encoding the polypeptides of, respectively, SEQ ID NO. 2 and SEQ ID NO. 4, or their substantial equivalents or their complementary sequences.

BRIEF DESCRIPTION OF THE DRAWINGS

These and other embodiments, features, and advantages of the invention will become better understood when considered in light of the following detailed description and appended drawings, wherein.

DETAILED DESCRIPTION OF THE INVENTION

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices, and materials are now described.

All publications mentioned herein and in the Appendix are incorporated by reference herein for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

Figure 1:
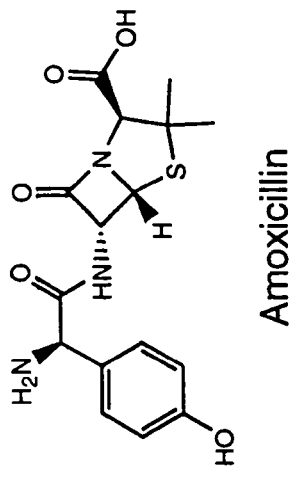
FIG. 1 depicts two semisynthetic antibiotics made with D-amino acids (D-amino acid portion in bold)
Figure 2:
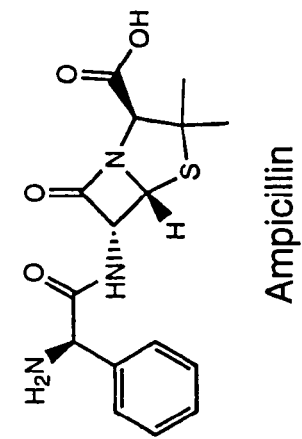
FIG. 2 depicts the structure of the D-cyclohexylalanine-containing drug Inogatran (D-amino acid portion in bold)
Figure 2:
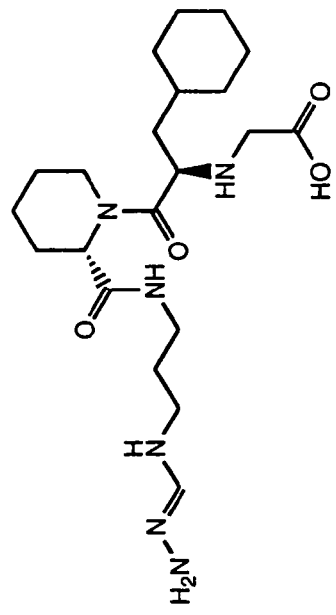
Figures 3, 4:
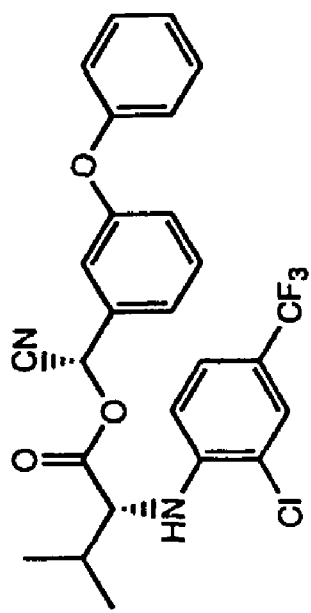
FIG. 3 lists the components of the D-amino acid-containing decapeptide drug Cetrorelix (D-amino acids in bold)
FIG. 4 depicts the structure of the D-valine-containing pyrethroid insecticide Fluvalinate (D-amino acid portion in bold)
Figure 5:
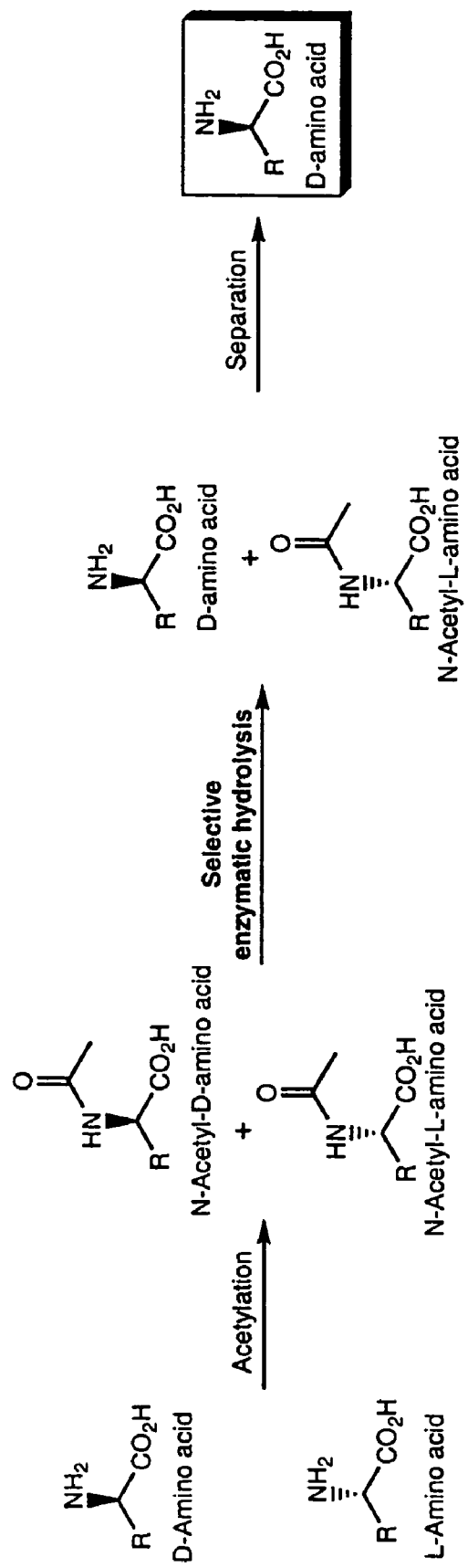
FIG. 5 is a schematic illustration of the prior art enzymatic resolution method (using an amidase) of making D-amino acids.
Figure 6:
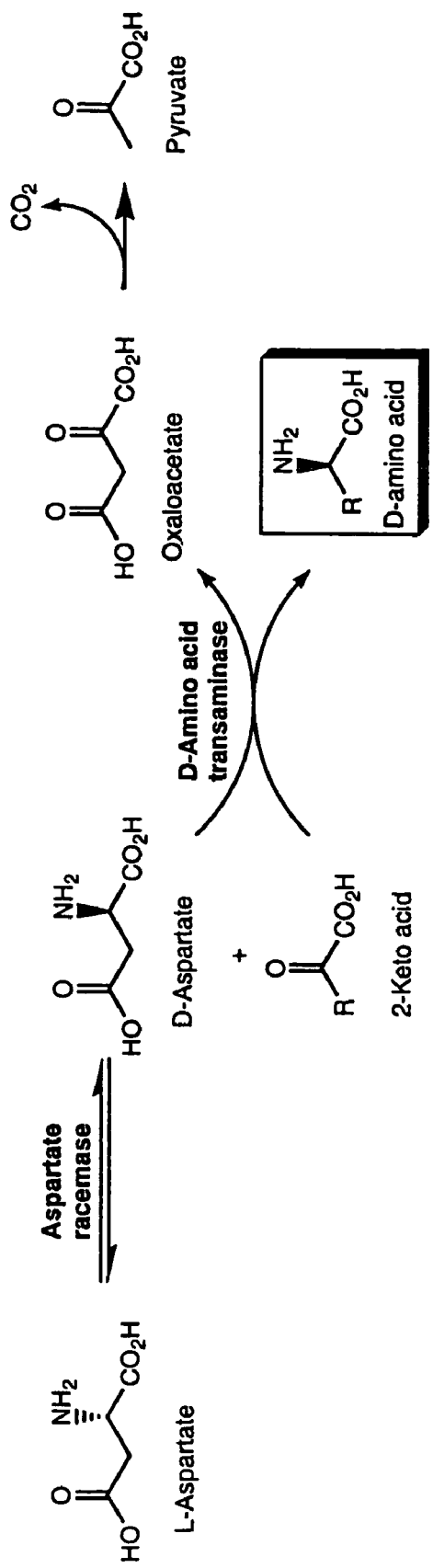
FIG. 6 is a schematic illustration of the prior art method of making D-amino acids via the transaminase reaction.
Figure 7:
FIG. 7 is a schematic illustration of the prior art D-hydantoinase/D-carbamoylase system for making D-amino acids.
Figure 8:
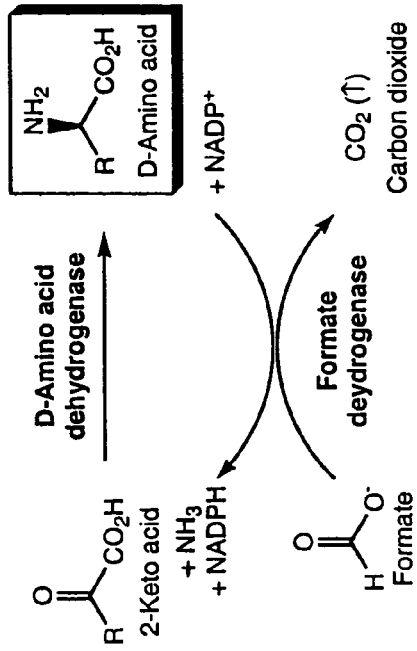
FIG. 8 is a schematic illustration of the D-amino acid dehydrogenase system for making D-amino acids according to one embodiment of the present invention.

The present invention describes novel polypeptides capable of catalyzing the conversion of a 2-ketoacid to a D-amino acid, and their use in producing D-amino acids by reductive amination of the corresponding 2-ketoacid. Functionally, the polypeptides act as D-amino dehydrogenase enzymes, and the novel method is referred to as the D-amino acid dehydrogenase method for making D-amino acids. This method overcomes many of the drawbacks of the current methods employed to make D-amino acids. In this process, schematically illustrated in FIG. 8, a 2-ketoacid is aminated with ammonium or an ammonium source to form the D-amino acid. The enzyme requires a nicotinamide cofactor (NADPH or NADH), which is recycled with an appropriate nicotinamide cofactor recycle system. Such a nicotinamide cofactor recycle system can include an $NAD^+$ or $NADP^+$-dependent formate dehydrogenase using inexpensive formate as the reductant, an $NAD^+$ or $NADP^+$-dependent glucose dehydrogenase and glucose as the reductant or any other similar system. Advantageously, the reaction allows D-amino acids to be prepared in a single step, unlike the prior art methods for making D-amino acids. Other advantages of the method include the use of inexpensive, readily available starting materials, a 100% theoretical yield, a 100% enantiomeric excess of the D-amino acid, and no by-products (other than volatile $CO_2$) that must be removed in downstream purification steps. The net reaction, as shown in FIG. 8, is:

2-ketoacid+ammonium formate→D-amino acid+$CO_2$

The present invention is based on the discovery that certain mutated forms of the enzyme diaminopimelate dehydrogenase (DAPDH) from *Corynebacterium glutamicum* (ATTC #13032) are capable of catalyzing the stereoselective reductive amination of a 2-ketoacid to produce a D-amino acid. It is important to note that wild-type diaminopimelate dehydrogenase enzyme from *Corynebacterium glutamicum* has little or no activity toward the reductive amination of 2-ketoacids to produce D-amino acids, but the mutant enzymes that are described herein have this new catalytic activity. Within the scope of this invention, a number of mutations at different amino acid positions in the artificial enzyme have been produced and tested: Lys44, Phe83, Thr89, Gln151, Asp155, Thr170, Glu178, Arg196, Pro244, His245, His248, and Asn271. These positions have been found to be particularly important in creating the selectivity and breadth of scope for the reaction that produces D-amino acids from the corresponding 2-ketoacids. In particular, specific examples of catalytically active DAPDH mutations found from active clones from saturation mutagenesis and directed evolution include: Lys44Glu, Phe83Ile, Thr89Pro, Gln151Leu, Asp155Gly, Thr170Ile, Thr170Val, Glu178Lys, Arg196Met, Pro244Ser, His245Asn, His248Glu, and Asn271Ser. However, it will be understood that there are other substitutions, as well as sequences similar to the wild-type or artificial diaminopimelate dehydrogenase, that could be used as a starting point, and that there are therefore a number of similar mutant enzymes that will be substantial equivalents to the specific mutations described herein.

In the attached Sequence Listing, the native DAPDH ORF for the oligonucleotide sequence is shown as SEQ ID NO. 1 (DNA), with the encoded amino acid sequence shown as SEQ ID NO. 2. Mutants were generated in an artificial variant of DAPDH in which a ggt codon (glycine) was added to the 5' end of the native ORF to generate a restriction enzyme site. This DNA sequence is shown as SEQ ID NO. 3 (DNA) with the corresponding polypeptide shown as SEQ ID NO. 4. Mutant numbers refer to SEQ ID NO. 4.

BioCatalytics ID number and mutations are:
540: Thr170Ile, Arg196Met, His245Asn
574: Gln151Leu, Thr170Ile, Arg196Met, His245Asn
620: Phe83Ile, Gln151Leu, Thr170Ile, Arg196Met, His245Asn, Asn27Ser
621: Asp155Gly, Gln151Leu, Thr170Ile, Arg196Met, His245Asn
622: Gln151Leu, Thr170Val, Glu178 Lys, Arg196Met, His245Asn, His248Glu, Asn271Ser
623: Gln151Leu, Thr170Ile, Arg196Met, His245Asn, Asn271Ser
624: Thr89Pro, Gln151Leu, Thr170Ile, Arg196Met, His245Asn,
691: Lys44Glu, Gln151Leu, Thr170Ile, Arg196Met, Pro244Ser, His245Asn.

As used in this application in reference to a given polypeptide or oligonucleotide sequence, the term "substantial equivalent" means a sequence that is at least 80% homologous at the amino acid level to the reference sequence, where homology is determined using a BLAST program or a comparable methodology. Thus, a sequence that is at least 80% homologous to the sequence described in SEQ ID 4 is considered "substantially equivalent" to the diaminopimelate dehydrogenase artificial sequence, and a sequence that is at least 80% homologous to SEQ ID 2 but that incorporated at least one of the amino acid mutations at a location selected from the group comprised of Lys44, Phe83, Thr89, Gln151, Asp155, Thr170, Glu178, Arg196, Pro244, His245, His 248, and Asn271 is considered a "substantial equivalent" of the novel polypeptides described herein that catalyze the reductive amination of a 2-ketoacid to produce a D-amino acid. More preferably, the substantially equivalent sequence is at least 88% homologous to the reference sequence, and even more preferably still, the substantially equivalent sequence is at least 90% homologous to the reference sequence.

In another aspect of the invention, a method of producing a D-amino acid from the corresponding 2-ketoacid, using a novel polypeptide as described herein is provided. D-amino acid dehydrogenase enzymes have been made available for the first time through the methods and compositions described in the present invention. These novel polypeptides catalyze the reductive amination of a 2-ketoacid to produce the corresponding D-amino acid. The reaction takes place in the presence of the 2-ketoacid, ammonia or an ammonia source, and a nicotinamide cofactor. According to this aspect of the invention, the method comprises contacting a 2-ketoacid with a modified amino acid sequence (i.e., a polypeptide) or its substantial equivalent in the presence of a nicotinamide cofactor and ammonia or an ammonia source, to produce a D-amino acid.

Nonlimiting examples of ammonia sources include ammonium halides, such as ammonium chloride; other sources of ammonium ion; and reagents capable of generating ammonia or ammonium ion in situ.

In one embodiment of the invention the modified amino acid sequence is a modification of SEQ ID NO. 4 (attached), or its substantial equivalent, said modified amino acid sequence containing a replacement of at least one amino acid in SEQ ID NO. 4 selected from the group consisting of Lys44, Phe83, Thr89, Gln151, Asp155, Thr170, Glu178, Arg196, Pro244, His245, His 248, and Asn271.

In another embodiment of the invention, the modified amino acid sequence is a modification of SEQ ID NO. 4 (attached), or its substantial equivalent, said modified amino acid sequence containing at least one amino acid replacement in SEQ ID NO. 4 selected from the group consisting of Lys44Glu, Phe83Ile, Thr89Pro, Gln151Leu, Asp155Gly, Thr170Ile, Thr170Val, Glu178Lys, Arg196Met, Pro244Ser, His245Asn, His248Glu, and Asn271Ser.

Figure 9:
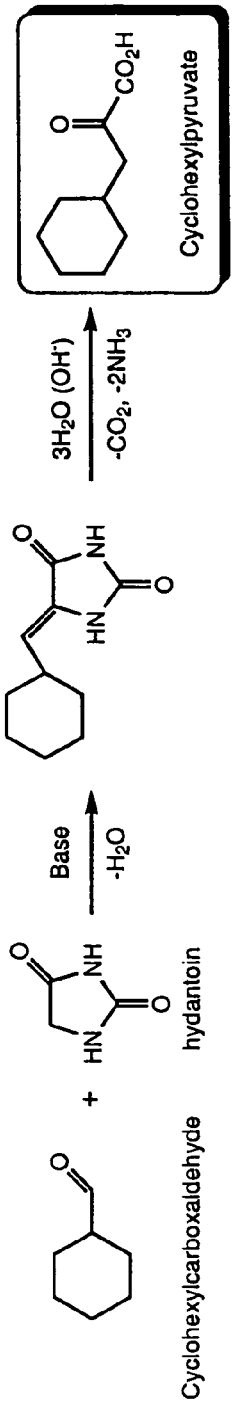
FIG. 9 depicts the synthesis of the starting material 2-ketoacid cyclohexylpyruvate.

To demonstrate the utility of a catalytically active polypeptide according to the invention (functionally, a "D-amino acid dehydrogenase"), the polypeptide was used to synthesize D-cyclohexylalanine on the gram scale. D-cyclohexylalanine was chosen as the substrate because it is a commercially useful D-amino acid (used in the thrombin inhibitor drug Inogatran) and the mutant D-amino acid dehydrogenase shows high activity towards it. The starting material, cyclohexylpyruvate, can be synthesized in high yield (>83% (Reference 16 in the Appendix)) from the corresponding aldehyde and hydantoin (both are very inexpensive reagents available in bulk) as shown in FIG. 9. This chemistry and many others (Ref. 17 in the Appendix) are available for the low-cost production of a wide range of 2-ketoacids.

Figure 10:
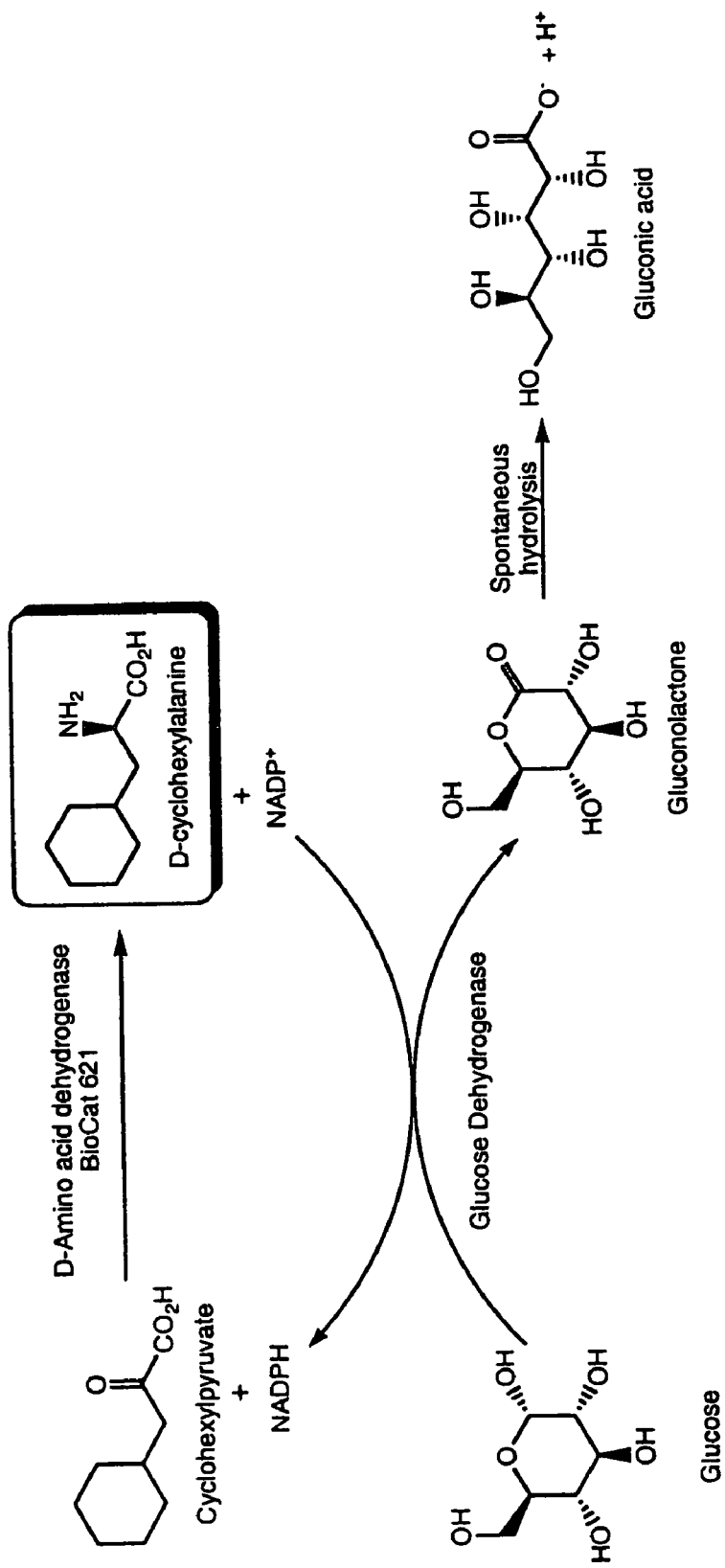
FIG. 10 is a schematic illustration of the reaction scheme for the gram-scale synthesis of D-cyclohexylalanine, according to one embodiment of the present invention.

In order to use the D-amino acid dehydrogenase for synthesis, the cofactor, NADPH, must be regenerated. It is not economically feasible to use NADPH in stoichiometric amounts. One method used for NADPH regeneration proceeds by the oxidation of glucose to gluconolactone, catalyzed by glucose dehydrogenase with the simultaneous reduction of $NADP^+$ to NADPH. The spontaneous hydrolysis of gluconolactone to gluconic acid is essentially irreversible and drives the reaction to completion. An alternative approach, currently under development at BioCatalytics, Inc. uses an $NADP^+$-dependent formate dehydrogenase that regenerates NADPH with the concomitant production of $CO_2$. This will likely prove to be an ideal method for NADPH recycle as it does not generate any recalcitrant by-products. BioCatalytics, Inc. (Pasadena, Calif.) produces a commercial glucose dehydrogenase, and this route was used for the NADPH cofactor regeneration. The reaction scheme for the gram scale synthesis of D-cyclohexylalanine is shown in FIG. 10.

The gram scale reaction was set up as follows:
Buffer: 25 ml of 100 mM sodium carbonate/bicarbonate, pH 9.0
Cyclohexylpyruvate: 1 g=40 g/L, 235 mM
$NH_4Cl$: 0.63 g=470 mM=2 molar excess to ketoacid
Glucose: 1.59 g=353 mM=1.5 molar excess to ketoacid
NADP+: 5.0 mg=0.23 mM=$\frac{1}{1000}^{th}$ molar excess to ketoacid
D-Amino acid dehydrogenase (BioCat 621 from BioCatalytics, Inc.):
10 mg=30 units@ 3 U/mg
Glucose dehydrogenase: 0.25 mg=25 units@ 100 U/mg Although the D-amino acid dehydrogenase requires NADPH, we started with $NADP^+$ as it is significantly cheaper and this is how the reaction would likely be performed industrially. An initial round of cofactor regeneration occurs before the D-amino acid dehydrogenase reaction begins. Although the glucose dehydrogenase produces an equivalent of acid, there was not a significant change in pH, due to the buffering effects of the sodium carbonate and the ammonium chloride. A slightly lower amount of glucose dehydrogenase units was used relative to the D-amino acid dehydrogenase units in order to keep most of the cofactor in the oxidized form where it is more stable versus the reduced form. The amount of cofactor used was $\frac{1}{1000}^{th}$ the amount of substrate on a molar basis. While this is a respectable ratio, we have routinely achieved higher recycle ratios, greater than 5000:1, in the laboratory.

Periodically, an aliquot of the reaction was removed and the formed amino acid was derivatized with FMOC (for UV detection) and analyzed via HPLC. It appeared that after 2 hours one of the enzymes, probably the D-amino acid dehydrogenase, lost activity. This could be due to enzyme inhibition by the product or enzyme inactivation. More enzyme was added and this was repeated after 4.5 hours. By 7 hours the reaction was completed.

After the reaction was completed, the pH of the solution was lowered to pH 6 (the approximate pI of cyclohexylalanine) causing the amino acid to precipitate from the solution. The solids were collected, washed with cold water and dried overnight in a vacuum oven. The isolated yield was approximately 70%.

Figure 11A:
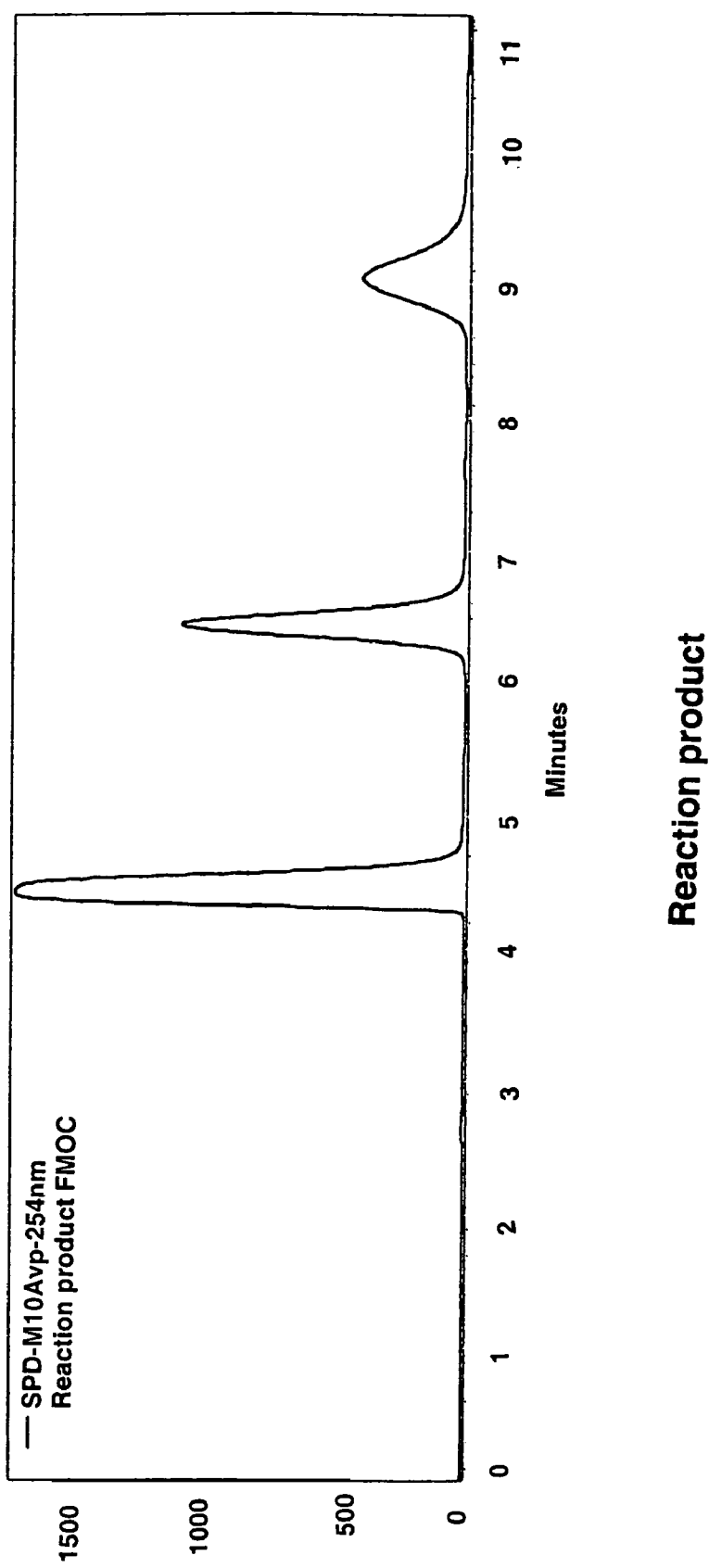
FIG. 11A is a chromatogram of cyclohexylalanine ("Reaction product") produced according to one embodiment of the invention.
Figure 11:
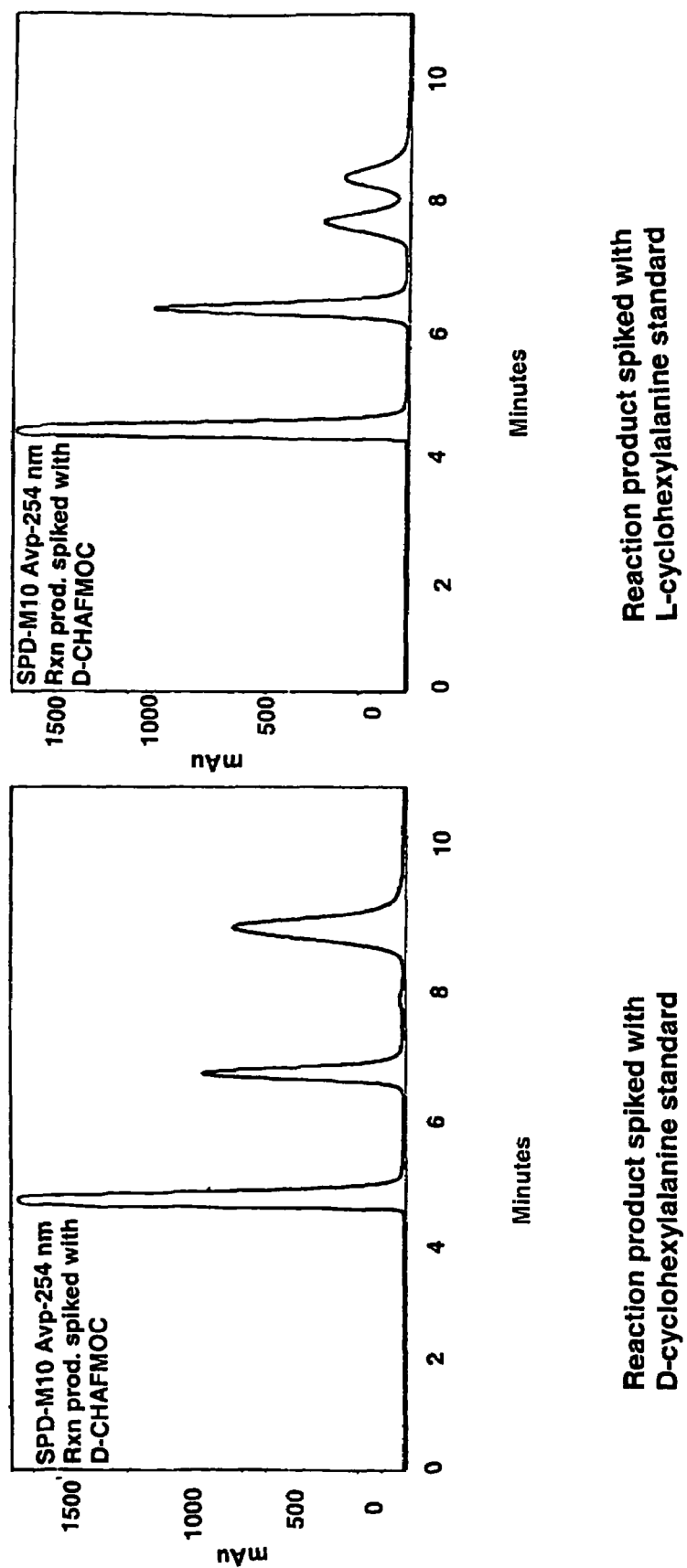
FIG. 11B is a pair of chromatograms for cyclohexylalanine: The one on the left is for the reaction product spiked with D-cyclohexylalanine standard, while the one on the right is for the reaction product spiked with L-cyclohexylalanine standard. The first two peaks in the chromatograms in FIGS. 11A and 11B result from the FMOC reagent used to derivatize the products.

To determine product stereochemistry, the product was analyzed via chiral HPLC. A Chirobiotic T column (Astec, Whippany, N.J.) was used to separate the enantiomers. FIG. 11 shows chromatographs of the reaction product, the reaction product spiked with a D-cyclohexylalanine standard, and the reaction product spiked with an L-cyclohexylalanine standard. As shown in the figure, the reaction product has only a single peak, corresponding to the D-enantiomer. No peak is observed where the L-enantiomer would be seen. This indicated the reaction product consists of nearly 100% the D-enantiomer.

Using other 2-ketoacids and an appropriate catalytically active polypeptide (a D-amino acid dehdyrogenase) as described herein, other D-amino acids are produced in a similar fashion, by contacting the 2-ketoacid with the polypeptide in the presence of a nicotinamide cofactor and ammonia or an ammonia source. For example, D-phenylglycine is produced from benzoylformate; D-phenylalanine from phenylpyruvate; D-p-fluorophenylalanine from p-fluorophenylpyruvate; D-p-chlorophenylalanine from p-chlorophenylpyruvate; D-tyrosine from p-hydroxyphenylpyruvate; D-4-phenyl-2-aminobutanoate from 4-phenyl-2-ketobutanoate; D-valine from 2-ketoisovalerate; D-trpytophan from indolepyruvate; D-leucine from 2-ketoisohexanoate; D-2-aminooctanoate from 2-keto-octanoate; and so forth. As will be understood by those skilled in the art, many other analogous D-amino acids are produced in an exactly analogous manner using a D-amino acid dehydrogenase of the present invention, the appropriate 2-ketoacid, ammonia or an ammonia source, and a source of nicotinamide cofactor.

The following are nonlimiting examples of the invention.

EXAMPLE 1

Diaminopimelate dehydrogenase (DAPDH) mutants were prepared from the following sequences:

1. (SEQ ID 4):
MGTNIRVAIVGYGNLGRSVEKLIAKQPDMDLVGIFSRRATLDTKTPV

FDVADVDKHADDVDVLFLCMGSATDIPEQAPKFAQFACTVDTYDNHR

DIPRHRQVMNEAATAAGNVALVSTGWDPGMFSINRVYAAAVLAEHQQ

HTFWGPGLSQGHSDALRRIPGVQKAVQYTLPSEDALEKARRGEAGDL

TGKQTHKRQCFVVADAADHERIENDIRTMPDYFVGYEVEVNFIDEAT

FDSEHTGMPHGGHVITTGDTGGFNHTVEYILKLDRNPDFTASSQIAF

GRAAHRMKQQGQSGAFTVLEVAPYLLSPENLDDLIARDV

-continued 2. (SEQ ID 2):
MTNIRVAIVGYGNLGRSVEKLIAKQPDMDLVGIFSRRATLDTKTPVF

DVADVDKHADDVDVLFLCMGSATDIPEQAPKFAQFACTVDTYDNHRD

IPRHRQVMNEAATAAGNVALVSTGWDPGMFSINRVYAAAVLAEHQQH

TFWGPGLSQGHSDALRRIPGVQKAVQYTLPSEDALEKARRGEAGDLT

GKQTHKRQCFVVADAADHERIENDIRTMYDYFVGYEVEVNFIDEATF

DSEHTGMPHGGHVITTGDTGGFNHTVEYILKLDRNPDFTASSQIAFG

RAAHRMKQQGQSGAFTVLEVAPYLLSPENLDDLIARDV

EXAMPLE 2

Random Mutagenesis of the Entire DAPDH Gene

The DAPDH was mutagenized randomly over the entire gene using error prone PCR techniques. To accomplish this, 50 pmole of each primer that anneals to the pTrcHis2A vector flanking the DAPDH gene insert (forward:5'-GAGG-TATATATTATTGTATCG-3' and reverse: 5'-GATGATGAT-GATGGTCGACGG-3') and 0.1 µg DAPDH/pTrcHis2A plasmid DNA template were added to 1.5 mM $MnCl_2$, 5.5 mM $MgCl_2$, 0.2 mM dATP, 0.2 mM dGTP, 1.0 mM dCTP, 1.0 mM dTTP, 1× Taq polymerase PCR buffer and 2.5 units Taq polymerase. The thermal cycling parameters were 94° C. for 2 min (1 cycle), 94° C. for 45 s, 52° C. for 45 s, 72° C. for 90 s (30 cycles), and 72° C. for 10 min (1 cycle). The PCR products were digested with DpnI to remove template DNA. The PCR products were purified and digested with NcoI and XhoI. The digested products were then gel-purified and the DAPDH fragments were ligated into the similarly digested vector pTrcHis2A. Ligation mixtures were transformed into E. coli TOP10 cells by electroporation and selected on LB medium supplemented with 100 µg/ml ampicillin.

EXAMPLE 3

Saturation Mutagenesis at Specific Codons in the DAPDH Gene

For site-saturation mutagenesis a similar procedure was used as in Example 2. The PCR reaction included the same forward and reverse primers as in Example 2, internal oligos containing an NNN sequence at the codon to be saturated mutagenized with a 15 bp overlap on both sides of the NNN, 0.2 mM dNTP, and 5.5 mM $MgCl_2$. The thermal cycling parameters were identical to those used in Example 2, as was the PCR product purification. The multiple PCR products (0.2 µg/fragment) from this reaction were combined with a second PCR reaction containing 50 pmole of the same forward and reverse primers, 0.2 mM dNTP, and 5.5 mM $MgCl_2$. The thermocycling parameters were: 94° C. for 2 min (1 cycle), 94° C. for 45 s, 48° C. for 45 s, (10 cycles), 94° C. for 45 s, 52° C. for 45 s, 72° C. for 90 s (30 cycles), and 72° C. for 10 min (1 cycle). The final PCR product was ligated and transformed as described in Example 2.

EXAMPLE 4

Synthesis of 4-fluorophenyl-2-oxopropanoic acid

A mixture of 4-fluorobenzaldehyde (250 mmol), glycine (250 mmol), anhydrous sodium acetate (1.75 mol) and acetic anhydride (5 mol) was heated in a 1 L flask with reflux and stirring for 2 hours. The mixture was then poured over 3 L of crushed ice. The orange solid was collected by filtration and air dried.

The crude azlactone was suspended in acetone (300 ml) and water (120 ml) and heated to boil at which point all solids dissolved. The acetone was removed by distillation and the resulting brown suspension was diluted with 350 ml water, filtered hot and the undissolved solid was extracted with an additional 250 ml and 500 ml of boiling water. The filtrates were allowed to stand, during which time brown-yellow crystals formed. The crystals were collected via suction filtration and redissolved in 1 L of boiling water. Activated carbon was added and the mixture was filtered hot. The filtrate was cooled in an ice bath at which time yellow solids formed.

The yellow solid, fluorophenylacetamidoacrylic acid was refluxed for 3 hr with 250 ml of 1 M HCl. The mixture was then cooled and stored at 4° C. for 20 hrs during which time grayish solids formed. The gray solids were collected via suction filtration and dried under vacuum.

EXAMPLE 5

Synthesis of 4-chlorophenyl-2-oxopropanoic acid

The procedure of Example 4 was repeated except 4-chlorobenzaldehyde was used in place of 4-fluorobenzaldehyde.

EXAMPLE 6

Synthesis of 3-(naphthalen-2-yl)-2-oxopropanoic acid

The procedure of Example 4 was repeated except 2-naphthaldehyde was used in place of 4-fluorobenzaldehyde.

EXAMPLE 7

Synthesis of 2-oxo-3-(pyridin-2-yl)propanoic acid

The procedure of Example 4 was repeated except 3-pyridinecarboxaldehyde was used in place of 4-fluorobenzaldehyde.

EXAMPLE 8

Synthesis of 3-cyclohexyl-2-oxopropanoic acid

The procedure of Example 4 was repeated except cyclohexylcarboxaldehyde was used in place of 4-fluorobenzaldehyde.

EXAMPLE 9

Screening of Mutant Libraries for Enzymes with Increased Activity

Individual colonies were picked using an AutoGenesys robotic colony picker (AutoGen, Framingham, Mass.), into 384-well microtiter plates containing Terrific Broth (TB) media with 100 µg/ml ampilicillin and grown 16 h at 37° C. After growth the master plates were replicated into 384 well plates containing TB, 100 µg/ml ampilicillin, and 50 µM IPTG (to induce gene expression) and allowed to grow 16 hr at 30° C. Glycerol was added to the master plates (final concentration of 20%) and stored at −80° C. After 16 hr growth of the replicated plates, the plates were spun down and the supernatant was removed. To the cell pellet, the following was added (20 µl/well):

Buffer: 100 mM sodium carbonate/bicarbonate, pH 9.5
Lysozyme: 1 mg/ml
Triton X-100: 0.1%
D-Amino acid(s) to be screened: 20 mM each
$NADP^+$: 1 mM The plates were allowed to shake at 200 rpm. During this time the cells were lysed and the enzyme was allowed to react with the substrate. After 1 hr the indicating dye, Nitro Blue Tetrazolium (0.15 mg/ml final concentration) and the electron transfer agent, phenazine methosulfate (0.01 mg/ml final concentration) were added (20 µl/well). The plates were monitored visually for wells changing from pink to purple color. Those wells that turned purple faster than the majority of the wells on the plate were noted as being positives.

The D-amino acids screened included one or more of the following: D-alanine, D-2-aminobutyrate, D-2-aminopentanoate, D-2-aminohexanoate, D-2-aminoheptanoate, D-2-aminooctanoate, D-valine, D-tert-leucine, D-isoleucine, D-leucine, D-cyclopentylglycine, D-cyclohexylalanine, D-methionine, D-aspartate, D-glutamate, D-phenylglycine, D-phenylalanine, D-tyrosine, D-4-fluorophenylalanine, D-4-chlorophenylalanine, D-homophenylalanine.

EXAMPLE 10

Production and Purification of Mutant DAPDH Enzyme

The DAPDH expressing *E. coli* from Example 2 or Example 3 was grown up in 2.8 L baffled flasks containing 1.2 L TB and 100 µg/ml ampillicin. The flasks were incubated at 30° C. and shaken at 180 rpm. After approximately 18 hrs of growth, the cells were induced with 50 µM IPTG and continued to be incubated at 30° C. and shaken at 180 rpm for an additional 18 hrs. After this time the cells were harvested via centrifugation. The cells were resuspended with 4 ml of 50 mM potassium phosphate buffer, pH 7.5, 0.1 mM DTT, and 0.5 mM PMSF per gram of wet cell paste. Cells were lysed on the APV-1000 homogenizer (Invensys, Albertslund, Denmark) at 13,000 psi. The lysate was treated with 0.15% PEI (50-60 kDa molecular weight), 250 mM NaCl, and 50 mM sodium borate to flocculate nucleic acids and lipids, which were then removed by centrifugation. To the treated lysate, solid ammonium sulfate was added to give 45% saturation. After 20 min. of stirring, the solids were removed by centrifugation and discarded. The supernatant was brought up to 75% ammonium sulfate saturation and the solids were collected by centrifugation after 20 min. of stirring. The pellet was redissolved in 70 ml of 25 mM potassium phosphate buffer, pH 7.5 and ultrafiltrated against 1 L of the same buffer at 4° C. The ultrafiltrated solution was lyophilized and the enzyme was stored at 4° C.

EXAMPLE 11

Activity Assay of Mutant DAPDH Enzyme for Reductive Amination of 2-Keto Acids

The mutant DAPDH enzyme was assayed spectrophotometrically by monitoring the decrease in concentration of NADPH. The typical reductive amination reaction contained the following: 100 mM sodium carbonate/bicarbonate buffer, pH 9.0, 200 mM $NH_4Cl$, 25 mM 2-keto acid, and 0.2 mM NADPH. The decrease in absorbance at 340 nm was monitored and an NADPH extinction coefficient of 6.22 $mM^{-1}cm^{-1}$ was used to correlate absorbance to concentration. Protein concentrations were determined via the Bradford method [19] using bovine serum albumin as a protein standard.

EXAMPLE 12

Activity Assay of Mutant DAPDH Enzyme for Oxidative Deamination of D-Amino Acids The mutant DAPDH enzyme was assayed spectrophotometrically by monitoring the increase in concentration of NADPH. The assay contained 100 mM sodium carbonate/bicarbonate buffer, pH 9.5, 25 mM D-amino acid, and 1 mM $NADP^+$. The increase in absorbance at 340 nm was followed and an extinction coefficient of 6.22 $mM^{-1}cm^{-1}$ was used to correlate absorbance to concentration. Protein concentrations were determined via the Bradford method using bovine serum albumin as a protein standard.

EXAMPLE 13

Synthesis of D-cyclohexylalanine Using Mutant DAPDH Enzyme

D-Cyclohexylalanine was synthesized by combining the following:
Buffer: 25 ml of 100 mM sodium carbonate/bicarbonate, pH 9.0
Cyclohexylpyruvate: 1 g (40 g/L, 235 mM)
$NH_4Cl$: 0.63 g (25.2 g/L, 475 mM)
Glucose: 1.6 g (64 g/L, 355 mM)
$NADP^+$: 5.0 mg (0.2 g/L, 0.25 mM)
Mutant DAPDH: 20 mg (0.8 mg/ml)
Glucose dehydrogenase: 0.25 mg (0.01 mg/ml)

The solution was allowed to mix at room temperature. The solution turned cloudy as the reaction proceeded indicating the production of insoluble D-cyclohexylalanine. After ~6 hours, the pH of the solution was lowered to pH 6 causing much of the D-cyclohexylalanine to precipitate. The resulting D-cyclohexylalanine was filtered and washed with cold water and dried in a vacuum oven for 24 hrs. The conversion of substrate was >95% determined via HPLC, however the isolated yield was ~70%. The D-cyclohexylalanine product was dissolved in pH 10 borate buffer and derivitized with FMOC-Cl according to the instructions provided with the reagent. The optical purity of the product was determined by chiral HPLC. The enantiomers were separated on a Chirobiotic T column (Astec, Whippany, N.J.). The column dimensions were 250×4.6 mm, with a 5 µm particle size. Separation was obtained via isocratic elution with 1 ml/min of 1:1:0.01:0.01 methanol:water:triethylamine:acetic acid. L-Cyclohexylalanine eluted at 7.8 min, D-cyclohexylalanine eluted at 8.6 min.

EXAMPLE 14

Synthesis of Other D-Amino Acids Using Mutant DAPDH Enzyme

Example 13 was repeated for the synthesis of other D-amino acids except the 2-keto acid was changed from cyclohexylpyruvate to one of the following: pyruvate, 2-oxobutyrate, 2-oxopentonate, 2-oxohexanoate, 2-oxoheptanoate, 2-oxooctanoate, 3-methyl-2-oxobutanoate, 4-methyl-2-oxopentanoate, 3-methyl-2-oxopentanoate, 2-cyclopentyl-2-oxoacetate, 4-(methylthio)-2-oxobutanoate, 2-oxoglutarate, phenylpyruvate, 4-hydroxyphenylpyruvate, 4-chlorophenylpyruvate, 4-fluorophenylpyruvate.

EXAMPLE 15

Synthesis of D-Amino Acids Using Mutant DAPDH Enzyme Coupled with NADP-Active Formate Dehdyrogenase Example 13 was repeated except glucose and glucose dehydrogenase was replaced with formate and NADP-active formate dehydrogenase, respectively.

EXAMPLE 16

Synthesis of Other D-Amino Acids Using Mutant DAPDH Enzyme and Ion Exchange Resin to Purify and Isolate the D-Amino Acid Example 14 was repeated but instead of using pH changes to purify and isolate the D-amino acid, the D-amino acid was instead purified and isolated using cation or anion ion exchange resin.

While this invention has been described in detail with reference to a certain preferred embodiments, it should be appreciated that the present invention is not limited to those precise embodiments. Rather, in view of the present disclosure which describes the current best mode for practicing the invention, many modifications and variations would present themselves to those of skill in the art without departing from the scope and spirit of this invention.

Moreover, this invention is not limited to the particular methodology, protocols, cell lines, animal species or genera, constructs, and reagents described as such may vary, as will be appreciated by one of skill in the art. The scope of the invention is, therefore, indicated by the following claims rather than by the foregoing description. All changes, modifications, and variations coming within the meaning and range of equivalency of the claims are to be considered within their scope.

---

What is claimed is:

1. A polypeptide at least 90% homologous with SEQ ID NO:2, said polypeptide capable of catalyzing the conversion of a 2-ketoacid into a D-amino acid and containing a replacement of at least one amino acid in SEQ ID NO: 2 selected from the group consisting of Lys43, Phe82, Thr88, Gln150, Asp154, Thr169, Glu177, Arg195, Pro243, His244, His247, and Asn270.

2. A polypeptide at least 90% homologous with SEQ ID NO: 2, said polypeptide capable of catalyzing the conversion of a 2-ketoacid into a D-amino acid and containing at least one amino acid replacement in SEQ ID NO: 2 selected from the group consisting of Lys43Glu, Phe82Ile, Thr88Pro, Gln150Leu, Asp154Gly, Thr169Ile, Thr169Val, Glu177Lys, Arg195Met, Pro243Ser, His244Asn, His247Glu, and Asn270Ser.

3. A polypeptide at least 90% homologous with SEQ ID NO: 4, said polypeptide capable of catalyzing the conversion of a 2-ketoacid into a D-amino acid and containing a replacement of at least one amino acid in SEQ ID NO: 4 selected from the group consisting of Lys44, Phe83, Thr89, Gln151, Asp155, Thr170, Glu178, Arg196, Pro244, His245, His248, and Asn271.

4. A polypeptide at least 90% homologous with SEQ ID NO: 4, said polypeptide capable of catalyzing the conversion of a 2-ketoacid into a D-amino acid and containing at least one amino acid replacement in SEQ ID NO: 4 selected from the group consisting of Lys44Glu, Phe83Ile, Thr89Pro, Gln151Leu, Asp155Gly, Thr170Ile, Thr170Val, Glu178Lys, Arg196Met, Pro244Ser, His245Asn, His248Glu, and Asn271Ser.

5. The polypeptide of claim 4, wherein the polypeptide comprises the amino acid replacements Thr170Ile, Arg196Met, and His245Asn.

6. The polypeptide of claim 4, wherein the polypeptide comprises the amino acid replacements Gln151Leu, Thr170Ile, Arg196Met, and His245Asn.

7. The polypeptide of claim 4, wherein the polypeptide comprises the amino acid replacements Phe83Ile, Gln151Leu, Thr170Ile, Arg196Met, His245Asn, and Asn271Ser.

8. The polypeptide of claim 4, wherein the polypeptide comprises the amino acid replacements Gln151Leu, Asp155Gly, Thr170Ile, Arg196Met, and His245Asn.

9. The polypeptide of claim 4, wherein the polypeptide comprises the amino acid replacements Gln151Leu, Thr170Ile, Arg196Met, His245Asn, and Asn271Ser.

10. The polypeptide of claim 4, wherein the polypeptide comprises the amino acid replacements Thr89Pro, Gln151Leu, Thr170Ile, Arg196Met, Pro244Ser, and His245Asn.

11. The polypeptide of claim 4, wherein the polypeptide comprises the amino acid replacements Lys44Glu, Gln151Leu, Thr170Ile, Arg196Met, Pro244Ser, and His245Asn.

12. A method of making a D-amino acid, comprising: contacting a 2-ketoacid with the polypeptide recited in any one of claims 1-4 or 5-11 in the presence of a nicotinamide cofactor and ammonia or an ammonium salt, said polypeptide being capable of catalyzing conversion of the 2-ketoacid into its corresponding D-amino acid.

13. A method of making a D-amino acid, comprising: contacting a 2-ketoacid with the polypeptide recited in claim 5 in the presence of a nicotinamide cofactor and ammonia or ammonium salt, said polypeptide being capable of catalyzing conversion of the 2-ketoacid into its corresponding D-amino acid.

14. A method of making a D-amino acid, comprising: contacting a 2-ketoacid with the polypeptide recited in claim 6 in the presence of a nicotinamide cofactor and ammonia or an ammonium salt, said polypeptide being capable of catalyzing conversion of the 2-ketoacid into its corresponding D-amino acid.

15. A method of making a D-amino acid, comprising: contacting a 2-ketoacid with the polypeptide recited in claim 7 in the presence of a nicotinamide cofactor and ammonia or an ammonium salt, said polypeptide being capable of catalyzing conversion of the 2-ketoacid into its corresponding D-amino acid.

16. A method of making a D-amino acid, comprising: contacting a 2-ketoacid with the polypeptide recited in claim 8 in the presence of a nicotinamide cofactor and ammonia or an ammonium salt, said polypeptide being capable of catalyzing conversion of the 2-ketoacid into its corresponding D-amino acid.

17. A method as recited in claim 12, wherein the 2-ketoacid is selected from the group consisting of pyruvate, cyclohexylpyruvate, phenylpyruvate, 4-hydroxyphenylpyruvate, 4-chlorophenylpyruvate, 4-fluorophenylpyruvate, 4-phenyl-2-ketobutanoate, benzoylformate, 2-ketoisovalerate, indolepyruvate, 2-ketoisohexanoate, 2-keto-octanoate, 2-oxobutyrate, 2-oxopentonate, 2-oxohexanoate, 2-oxoheptanoate, 2-oxooctanoate, 3-methyl-2-oxobutanoate, 4-methyl-2-oxopentanoate, 3-methyl-2-oxopentanoate, 2-cyclopentyl-2-oxoacetate, 4-(methylthio)-2-oxobutanoate, and 2-oxoglutarate.

18. A method as recited in claim 12, wherein the ammonium salt comprises ammonium chloride.

19. A method of making a D-amino acid, comprising: contacting a 2-ketoacid with the polypeptide recited in claim 9 in the presence of a nicotinamide cofactor and ammonia or an ammonium salt, said polypeptide being capable of catalyzing conversion of the 2-ketoacid into its corresponding D-amino acid.

20. A method of making a D-amino acid, comprising: contacting a 2-ketoacid with the polypeptide recited in claim 10 in the presence of a nicotinamide cofactor and ammonia or an ammonium salt, said polypeptide being capable of catalyzing conversion of the 2-ketoacid into its corresponding D-amino acid.

21. A method of making a D-amino acid, comprising: contacting a 2-ketoacid with the polypeptide recited in claim 11 in the presence of a nicotinamide cofactor and ammonia or an ammonium salt, said polypeptide being capable of catalyzing conversion of the 2-ketoacid into its corresponding D-amino acid.

* * * * *

SEQUENCE LISTING

<160> NUMBER OF SEQ ID NOS: 4

<210> SEQ ID NO 1
<211> LENGTH: 963
<212> TYPE: DNA
<213> ORGANISM: Corynebacterium glutamicum

<400> SEQUENCE: 1
atgaccaaca tccgcgtagc tatcgtgggc tacggaaacc tgggacgcag cgtcgaaaag    60

-continued

```
cttattgcca agcagcccga catggacctt gtaggaatct tctcgcgccg ggccaccctc      120
gacacaaaga cgccagtctt tgatgtcgcc gacgtggaca agcacgccga cgacgtggac      180
gtgctgttcc tgtgcatggg ctccgccacc gacatccctg agcaggcacc aaagttcgcg      240
cagttcgcct gcaccgtaga cacctacgac aaccaccgcg acatcccacg ccaccgccag      300
gtcatgaacg aagccgccac cgcagccggc aacgttgcac tggtctctac cggctgggat      360
ccaggaatgt tctccatcaa ccgcgtctac gcagcggcag tcttagccga gcaccagcag      420
cacaccttct ggggcccagg tttgtcacag ggccactccg atgctttgcg acgcatccct      480
ggcgttcaaa aggcagtcca gtacaccctc ccatccgaag acgccctgga aaaggcccgc      540
cgcggcgaag ccggcgacct taccggaaag caaacccaca gcgccaatg cttcgtggtt      600 gccgacgcgg ccgatcacga gcgcatcgaa acgacatcc gcaccatgcc tgattacttc      660
gttggctacg aagtcgaagt caacttcatc gacgaagcaa ccttcgactc cgagcacacc      720
ggcatgccac acggtggcca cgtgattacc accggcgaca ccggtggctt caaccacacc      780
gtggaataca tcctcaagct ggaccgaaac ccagatttca ccgcttcctc acagatcgct      840
ttcggtcgcg cagctcaccg catgaagcag cagggccaaa gcggagcttt caccgtcctc      900
gaagttgctc catacctgct ctccccagag aacttggacg atctgatcgc acgcgacgtc      960
taa                                                                   963
```

<210> SEQ ID NO 2
<211> LENGTH: 320
<212> TYPE: PRT
<213> ORGANISM: Corynebacterium glutamicum

<400> SEQUENCE: 2

```
Met Thr Asn Ile Arg Val Ala Ile Val Gly Tyr Gly Asn Leu Gly Arg
1               5                   10                  15

Ser Val Glu Lys Leu Ile Ala Lys Gln Pro Asp Met Asp Leu Val Gly
        20                  25                  30

Ile Phe Ser Arg Arg Ala Thr Leu Asp Thr Lys Thr Pro Val Phe Asp
    35                  40                  45

Val Ala Asp Val Asp Lys His Ala Asp Val Asp Val Leu Phe Leu
50                  55                  60

Cys Met Gly Ser Ala Thr Asp Ile Pro Glu Gln Ala Pro Lys Phe Ala
65                  70                  75                  80

Gln Phe Ala Cys Thr Val Asp Tyr Asp Asn His Arg Asp Ile Pro
        85                  90                  95

Arg His Arg Gln Val Met Asn Glu Ala Ala Thr Ala Ala Gly Asn Val
    100                 105                 110

Ala Leu Val Ser Thr Gly Trp Asp Pro Gly Met Phe Ser Ile Asn Arg
    115                 120                 125

Val Tyr Ala Ala Ala Val Leu Ala Glu His Gln Gln His Thr Phe Trp
130                 135                 140

Gly Pro Gly Leu Ser Gln Gly His Ser Asp Ala Leu Arg Arg Ile Pro
145                 150                 155                 160

Gly Val Gln Lys Ala Val Gln Tyr Thr Leu Pro Ser Glu Asp Ala Leu
            165                 170                 175

Glu Lys Ala Arg Arg Gly Glu Ala Gly Asp Leu Thr Gly Lys Gln Thr
        180                 185                 190

His Lys Arg Gln Cys Phe Val Val Ala Asp Ala Ala Asp His Glu Arg
    195                 200                 205
```

```
Ile Glu Asn Asp Ile Arg Thr Met Pro Asp Tyr Phe Val Gly Tyr Glu
210                 215                 220

Val Glu Val Asn Phe Ile Asp Glu Ala Thr Phe Asp Ser Glu His Thr
225                 230                 235                 240

Gly Met Pro His Gly Gly His Val Ile Thr Thr Gly Asp Thr Gly Gly
245                 250                 255

Phe Asn His Thr Val Glu Tyr Ile Leu Lys Leu Asp Arg Asn Pro Asp
260                 265                 270

Phe Thr Ala Ser Ser Gln Ile Ala Phe Gly Arg Ala Ala His Arg Met
275                 280                 285

Lys Gln Gln Gly Gln Ser Gly Ala Phe Thr Val Leu Glu Val Ala Pro
290                 295                 300

Tyr Leu Leu Ser Pro Glu Asn Leu Asp Asp Leu Ile Ala Arg Asp Val
305                 310                 315                 320
```

<210> SEQ ID NO 3
<211> LENGTH: 966
<212> TYPE: DNA
<213> ORGANISM: Artificial sequence
<220> FEATURE:
<223> OTHER INFORMATION: Chemically synthesized

<400> SEQUENCE: 3

```
atgggtacca acatccgcgt agctatcgtg ggctacggaa acctgggacg cagcgtcgaa      60
aagcttattg ccaagcagcc cgacatggac cttgtaggaa tcttctcgcg ccgggccacc     120
ctcgacacaa agacgccagt ctttgatgtc gccgacgtgg acaagcacgc cgacgacgtg     180
gacgtgctgt tcctgtgcat gggctccgcc accgacatcc tgagcaggc accaaagttc      240
gcgcagttcg cctgcaccgt agacacctac gacaaccacc gcgacatccc acgccaccgc     300
caggtcatga cgaagccgc caccgcagcc ggcaacgttg cactggtctc taccggctgg     360
gatccaggaa tgttctccat caaccgcgtc tacgcagcgg cagtcttagc cgagcaccag     420
cagcacacct tctggggccc aggtttgtca cagggccact ccgatgcttt cgacgcatc      480
cctggcgttc aaaaggcagt ccagtacacc ctcccatccg aagacgccct ggaaaaggcc     540
cgccgcggcg aagccggcga ccttaccgga aagcaaaccc acaagcgcca atgcttcgtg     600
gttgccgacg cggccgatca cgagcgcatc gaaaacgaca tccgcaccat gcctgattac     660
ttcgttggct acgaagtcga agtcaacttc atcgacgaag caaccttcga ctccgagcac     720
accggcatgc cacacggtgg ccacgtgatt accaccggcg acaccggtgg cttcaaccac     780
accgtggaat acatcctcaa gctggaccga aacccagatt tcaccgcttc ctcacagatc     840
gctttcggtc gcgcagctca ccgcatgaag cagcagggcc aaagcggagc tttcaccgtc     900
ctcgaagttg ctccatacct gctctcccca gagaacttgg acgatctgat cgcacgcgac     960
gtctaa                                                                966
```

<210> SEQ ID NO 4
<211> LENGTH: 321
<212> TYPE: PRT
<213> ORGANISM: Artificial Sequence
<220> FEATURE:
<223> OTHER INFORMATION: Chemically synthesized

<400> SEQUENCE: 4

```
Met Gly Thr Asn Ile Arg Val Ala Ile Val Gly Tyr Gly Asn Leu Gly
1               5                   10                  15
```

-continued

```
Arg Ser Val Glu Lys Leu Ile Ala Lys Gln Pro Asp Met Asp Leu Val
 20              25                  30

Gly Ile Phe Ser Arg Arg Ala Thr Leu Asp Thr Lys Thr Pro Val Phe
 35              40                  45

Asp Val Ala Asp Val Asp Lys His Ala Asp Asp Val Asp Val Leu Phe
 50              55                  60

Leu Cys Met Gly Ser Ala Thr Asp Ile Pro Glu Gln Ala Pro Lys Phe
 65              70                  75              80

Ala Gln Phe Ala Cys Thr Val Asp Thr Tyr Asp Asn His Arg Asp Ile
 85              90                  95

Pro Arg His Arg Gln Val Met Asn Glu Ala Ala Thr Ala Ala Gly Asn
100             105                 110

Val Ala Leu Val Ser Thr Gly Trp Asp Pro Gly Met Phe Ser Ile Asn
115             120                 125

Arg Val Tyr Ala Ala Ala Val Leu Ala Glu His Gln Gln His Thr Phe
130             135                 140

Trp Gly Pro Gly Leu Ser Gln Gly His Ser Asp Ala Leu Arg Arg Ile
145             150                 155             160

Pro Gly Val Gln Lys Ala Val Gln Tyr Thr Leu Pro Ser Glu Asp Ala
165             170                 175

Leu Glu Lys Ala Arg Arg Gly Glu Ala Gly Asp Leu Thr Gly Lys Gln
180             185                 190

Thr His Lys Arg Gln Cys Phe Val Val Ala Asp Ala Ala Asp His Glu
195             200                 205

Arg Ile Glu Asn Asp Ile Arg Thr Met Pro Asp Tyr Phe Val Gly Tyr
210             215                 220

Glu Val Glu Val Asn Phe Ile Asp Glu Ala Thr Phe Asp Ser Glu His
225             230                 235             240

Thr Gly Met Pro His Gly Gly His Val Ile Thr Thr Gly Asp Thr Gly
245             250                 255

Gly Phe Asn His Thr Val Glu Tyr Ile Leu Lys Leu Asp Arg Asn Pro
260             265                 270

Asp Phe Thr Ala Ser Ser Gln Ile Ala Phe Gly Arg Ala Ala His Arg
275             280                 285

Met Lys Gln Gln Gly Gln Ser Gly Ala Phe Thr Val Leu Glu Val Ala
290             295                 300

Pro Tyr Leu Leu Ser Pro Glu Asn Leu Asp Asp Leu Ile Ala Arg Asp
305             310                 315             320

Val
```